(12) United States Patent  (10) Patent No.: US 7,691,053 B2
Viola  (45) Date of Patent: Apr. 6, 2010

(54) GASTRIC RESTRICTOR ASSEMBLY AND METHOD OF USE

(75) Inventor: Frank J. Viola, Sandy Hook, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 1325 days.

(21) Appl. No.: 11/133,597

(22) Filed: May 20, 2005

(65) Prior Publication Data

US 2006/0264981 A1  Nov. 23, 2006

(51) Int. Cl.
*A61B 17/08* (2006.01)

(52) U.S. Cl. .................... 600/37; 606/157; 606/151

(58) Field of Classification Search ............ 606/151, 606/153, 157, 158; 600/37; 128/885
See application file for complete search history.

(56) References Cited

U.S. PATENT DOCUMENTS

| | | | | |
|---|---|---|---|---|
| 2,245,030 | A | * | 6/1941 | Benjamin et al. ............... 251/7 |
| 3,147,754 | A | * | 9/1964 | Koessler ..................... 128/885 |
| 4,424,811 | A | * | 1/1984 | Groot ........................ 606/157 |
| 4,458,681 | A | * | 7/1984 | Hopkins ..................... 606/157 |
| 4,558,699 | A | * | 12/1985 | Bashour ..................... 606/157 |
| 5,549,621 | A | * | 8/1996 | Bessler et al. ............... 606/151 |
| 6,131,576 | A | * | 10/2000 | Davis ........................ 128/885 |
| 6,358,228 | B1 | | 3/2002 | Tubman et al. |
| 6,400,980 | B1 | | 6/2002 | Lemelson |
| 6,419,699 | B1 | | 7/2002 | Schuessler |
| 6,427,089 | B1 | | 7/2002 | Knowlton |
| 6,432,039 | B1 | | 8/2002 | Wardle |
| 6,432,040 | B1 | | 8/2002 | Meah |
| 6,449,512 | B1 | | 9/2002 | Boveja |
| 6,450,173 | B1 | | 9/2002 | Forsell |
| 6,450,946 | B1 | | 9/2002 | Forsell |
| 6,453,907 | B1 | | 9/2002 | Forsell |
| 6,454,698 | B1 | | 9/2002 | Forsell |
| 6,454,699 | B1 | | 9/2002 | Forsell |
| 6,454,700 | B1 | | 9/2002 | Forsell |
| 6,454,701 | B1 | | 9/2002 | Forsell |
| 6,454,785 | B2 | | 9/2002 | De Hoyos Garza |
| 6,460,543 | B1 | | 10/2002 | Forsell |
| 6,461,292 | B1 | | 10/2002 | Forsell |
| 6,461,293 | B1 | | 10/2002 | Forsell |
| 6,463,935 | B1 | | 10/2002 | Forsell |
| 6,464,698 | B1 | | 10/2002 | Falwell |
| 6,471,635 | B1 | | 10/2002 | Forsell |
| 6,494,879 | B2 | | 12/2002 | Lennox et al. |
| 6,500,110 | B1 | | 12/2002 | Davey et al. |
| 6,511,490 | B2 | | 1/2003 | Robert |
| 6,511,506 | B2 | | 1/2003 | Chevillon et al. |
| 6,540,789 | B1 | | 4/2003 | Silverman et al. |
| 6,543,456 | B1 | | 4/2003 | Freeman |

(Continued)

*Primary Examiner*—Charles A Marmor, II
*Assistant Examiner*—Catherine E Burk

(57) ABSTRACT

A gastric restrictor assembly is provided which includes a first longitudinal member, a second longitudinal member, a first connector and a second connector. The first and second connectors support the first and second longitudinal members in spaced relation. The second longitudinal member is rotatably supported between the first and second connectors and includes a bend or offset. The second longitudinal member is rotatable to rotate the offset in relation to the first longitudinal member to selectively vary the width of a channel defined between the first and second longitudinal members. In one embodiment, the second longitudinal member includes engagement structure for engaging a positioning tool and indexing structure for releasably securing the second longitudinal member at fixed positions of rotation in relation to the first longitudinal member.

17 Claims, 5 Drawing Sheets

U.S. PATENT DOCUMENTS

| | | |
|---|---|---|
| 6,547,801 B1 | 4/2003 | Dargent et al. |
| 6,558,400 B2 | 5/2003 | Deem et al. |
| 6,572,627 B2 | 6/2003 | Gabbay |
| 6,579,225 B2 | 6/2003 | Pregenzer et al. |
| 6,587,719 B1 | 7/2003 | Barrett et al. |
| 6,596,004 B1 | 7/2003 | Regnault |
| 6,609,025 B2 | 8/2003 | Barrett et al. |
| 6,627,206 B2 | 9/2003 | Lloyd |
| 6,652,448 B2 | 11/2003 | Migachyov |
| 6,656,194 B1 | 12/2003 | Gannoe et al. |
| 6,666,817 B2 | 12/2003 | Li |
| 6,675,809 B2 | 1/2004 | Stack et al. |
| 6,676,674 B1 | 1/2004 | Dudai |
| 6,726,696 B1 | 4/2004 | Houser et al. |
| 6,730,014 B2 | 5/2004 | Wilk |
| 6,740,121 B2 | 5/2004 | Geitz |
| 6,746,460 B2 | 6/2004 | Gannoe et al. |
| 6,752,754 B1 | 6/2004 | Feng et al. |
| 6,755,869 B2 | 6/2004 | Geitz |
| 6,758,219 B2 | 7/2004 | Sapala et al. |
| 6,773,440 B2 | 8/2004 | Gannoe et al. |
| 6,773,441 B1 | 8/2004 | Laufer et al. |
| 6,776,789 B2 | 8/2004 | Bryant et al. |
| 6,790,214 B2 | 9/2004 | Kraemer et al. |
| 6,802,868 B2 | 10/2004 | Silverman et al. |
| 6,808,483 B1 | 10/2004 | Ortiz et al. |
| 6,826,428 B1 | 11/2004 | Chen et al. |
| 2001/0011543 A1 | 8/2001 | Forsell |
| 2001/0034470 A1 | 10/2001 | Whalen et al. |
| 2002/0022851 A1 | 2/2002 | Kalloo et al. |
| 2002/0028979 A1 | 3/2002 | Silverman et al. |
| 2002/0052438 A1 | 5/2002 | Lau et al. |
| 2002/0065449 A1 | 5/2002 | Wardle |
| 2002/0091395 A1 | 7/2002 | Gabbay |
| 2002/0116013 A1 | 8/2002 | Gleason et al. |
| 2002/0151763 A1 | 10/2002 | Cook et al. |
| 2002/0169464 A1 | 11/2002 | Latour |
| 2002/0183768 A1* | 12/2002 | Deem et al. ............... 606/151 |
| 2002/0188354 A1 | 12/2002 | Peghini |
| 2002/0198548 A1 | 12/2002 | Robert |
| 2003/0032857 A1 | 2/2003 | Forsell |
| 2003/0040804 A1 | 2/2003 | Stack et al. |
| 2003/0040808 A1 | 2/2003 | Stack et al. |
| 2003/0088148 A1 | 5/2003 | Forsell |
| 2003/0092962 A1 | 5/2003 | Forsell |
| 2003/0109931 A1 | 6/2003 | Geitz |
| 2003/0120288 A1 | 6/2003 | Benchetrit |
| 2003/0130670 A1 | 7/2003 | Anderson et al. |
| 2003/0144575 A1 | 7/2003 | Forsell |
| 2003/0158564 A1 | 8/2003 | Benchetrit |
| 2003/0158569 A1 | 8/2003 | Wazne |
| 2003/0158601 A1 | 8/2003 | Silverman et al. |
| 2003/0171768 A1 | 9/2003 | McGhan |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208212 A1 | 11/2003 | Cigaina |
| 2003/0212306 A1 | 11/2003 | Banik |
| 2003/0225311 A1 | 12/2003 | Sayet et al. |
| 2004/0006351 A1 | 1/2004 | Gannoe et al. |
| 2004/0030347 A1 | 2/2004 | Gannoe et al. |
| 2004/0039452 A1 | 2/2004 | Bessler |
| 2004/0044357 A1 | 3/2004 | Gannoe et al. |
| 2004/0045562 A1 | 3/2004 | Sapala et al. |
| 2004/0049209 A1 | 3/2004 | Benchetrit |
| 2004/0059289 A1 | 3/2004 | Alvarez |
| 2004/0059354 A1* | 3/2004 | Smith et al. .............. 606/151 |
| 2004/0082963 A1 | 4/2004 | Gannoe et al. |
| 2004/0089313 A1 | 5/2004 | Utley et al. |
| 2004/0093091 A1 | 5/2004 | Gannoe et al. |
| 2004/0097989 A1 | 5/2004 | Trigueros |
| 2004/0107004 A1 | 6/2004 | Levine et al. |
| 2004/0116773 A1 | 6/2004 | Furness et al. |
| 2004/0117031 A1 | 6/2004 | Stack et al. |
| 2004/0122455 A1 | 6/2004 | Lin |
| 2004/0122456 A1 | 6/2004 | Saadat et al. |
| 2004/0122473 A1 | 6/2004 | Ewers et al. |
| 2004/0122526 A1 | 6/2004 | Imran |
| 2004/0133219 A1 | 7/2004 | Forsell |
| 2004/0138684 A1 | 7/2004 | Eton |
| 2004/0138760 A1 | 7/2004 | Schurr |
| 2004/0138761 A1 | 7/2004 | Stack et al. |
| 2004/0143342 A1 | 7/2004 | Stack et al. |
| 2004/0147810 A1 | 7/2004 | Mizuno |
| 2004/0158272 A1 | 8/2004 | Hofle et al. |
| 2004/0158331 A1 | 8/2004 | Stack et al. |
| 2004/0167561 A1 | 8/2004 | Boucher et al. |
| 2004/0172141 A1 | 9/2004 | Stack et al. |
| 2004/0172142 A1 | 9/2004 | Stack et al. |
| 2004/0199196 A1 | 10/2004 | Ravo |
| 2004/0204722 A1 | 10/2004 | Sikora et al. |
| 2004/0204768 A1 | 10/2004 | Geitz |
| 2004/0209538 A1 | 10/2004 | Klinge et al. |
| 2004/0210243 A1 | 10/2004 | Gannoe et al. |
| 2004/0220682 A1 | 11/2004 | Levine et al. |
| 2004/0230137 A1 | 11/2004 | Mouton |
| 2004/0243152 A1 | 12/2004 | Taylor et al. |
| 2004/0254537 A1 | 12/2004 | Conlon et al. |
| 2004/0260316 A1 | 12/2004 | Knudson et al. |
| 2004/0267293 A1 | 12/2004 | Byrum et al. |
| 2005/0004430 A1 | 1/2005 | Lee et al. |
| 2005/0004681 A1 | 1/2005 | Stack et al. |
| 2005/0038458 A1 | 2/2005 | Bailly et al. |
| 2005/0049718 A1 | 3/2005 | Dann et al. |
| 2005/0055039 A1 | 3/2005 | Burnett et al. |
| 2005/0070931 A1 | 3/2005 | Li et al. |
| 2005/0075652 A1 | 4/2005 | Byrum et al. |
| 2005/0080317 A1 | 4/2005 | Merade |
| 2005/0085688 A1 | 4/2005 | Girard et al. |
| 2005/0085835 A1* | 4/2005 | Rennich .................... 606/157 |
| 2005/0085923 A1 | 4/2005 | Levine et al. |
| 2005/0090844 A1 | 4/2005 | Patel et al. |

* cited by examiner

GASTRIC RESTRICTOR ASSEMBLY AND METHOD OF USE

BACKGROUND

1. Technical Field

The present disclosure relates to a surgical implant for treating obesity in a patient. More particularly, the present disclosure relates to a surgical implant for constricting the stomach of a patient to treat obesity in a patient.

2. Background of Related Art

A variety of different approaches are known for the treatment of obesity in a patient. These approaches can be of the nonsurgical variety, e.g., dieting, or of the surgical variety, e.g., gastric bypass, small bowel bypass etc. Where non-invasive non-surgical procedures such as dieting rely on the will power of a patient and may not be effective, invasive surgical procedures such as bypass surgery can be risky and have undesirable side effects. As such, less invasive surgical devices for constricting or reducing the capacity of the stomach have been developed. These devices include gastric bands which are positioned about the stomach to constrict the stomach and devices such as inflatable balloons for reducing the reservoir capacity of the stomach. Each of these types of devices produce a sense of satiety in a patient to reduce the patient's desire to ingest food.

Although the above-identified devices have had some success, improvements to these devices would be desirable.

SUMMARY

In accordance with the present disclosure, a gastric restrictor assembly is provided which includes a first longitudinal member, a second longitudinal member, a first connector and a second connector. The first longitudinal member can be substantially rigid and defines a first longitudinal axis. The second longitudinal member can also be rigid and includes a bend or offset formed therein. The second longitudinal member defines a second longitudinal axis. In one embodiment, the bend or offset includes first and second or offsetting or angled portions and a base portion defining a third longitudinal axis which is spaced from the second longitudinal axis such that the bend and the second longitudinal axis define a recess. Alternately, other bend configurations are envisioned.

The first connector includes first and second bores for rotatably receiving first ends of the first and second longitudinal members. In one embodiment, each first end of the first and second longitudinal members includes an annular groove. A pair of pins is provided to extend through a pair of openings formed in the first connector to rotatably secure the first ends of the first and second longitudinal members within first and second bores of the first connector. The second connector also includes first and second bores for rotatably receiving second ends of the first and second longitudinal members. The second ends of the first and second longitudinal members may also include an annular groove for receiving a pin for rotatably fastening the second ends of the first and second longitudinal members within the first and second bores of the second connector. Alternately, the first longitudinal member can be non-rotatably secured between the first and second connectors.

The first and second connectors support the first and second longitudinal members in spaced relation to define a channel therebetween. The second longitudinal member is rotatably supported between the first and second connectors. In one embodiment, the first end of the second longitudinal member includes engagement structure for engaging a positioning tool. The positioning tool effects rotation of the second longitudinal member about the second longitudinal axis to selectively change the angular position of the bend in relation to the first longitudinal member to selectively change the width of the channel defined between the first and second longitudinal members.

In one embodiment, the first end of the second longitudinal member includes indexing structure for engaging indexing structure formed within a bore of the first connector. The indexing structure may include one or more detents positioned on the second longitudinal member or first connector which are configured to be releasably received within one or more grooves formed in the other of the second longitudinal member and first connector. Alternately, the indexing structure may be provided on the second connector end of the device. The indexing structure releasably secures the second longitudinal member at a fixed position of rotation in relation to the first longitudinal member until a predetermined torque is applied to the second longitudinal member such as by the positioning tool.

BRIEF DESCRIPTION OF THE DRAWINGS

Various embodiments of the presently disclosed gastric restrictor assembly are disclosed herein with reference to the drawings, wherein.

DETAILED DESCRIPTION OF EMBODIMENTS

Embodiments of the presently disclosed gastric restrictor assembly and its method of use will now be described in detail with reference to the drawings in which like numerals designate identical or corresponding elements in each of the several views.

Figure 1:
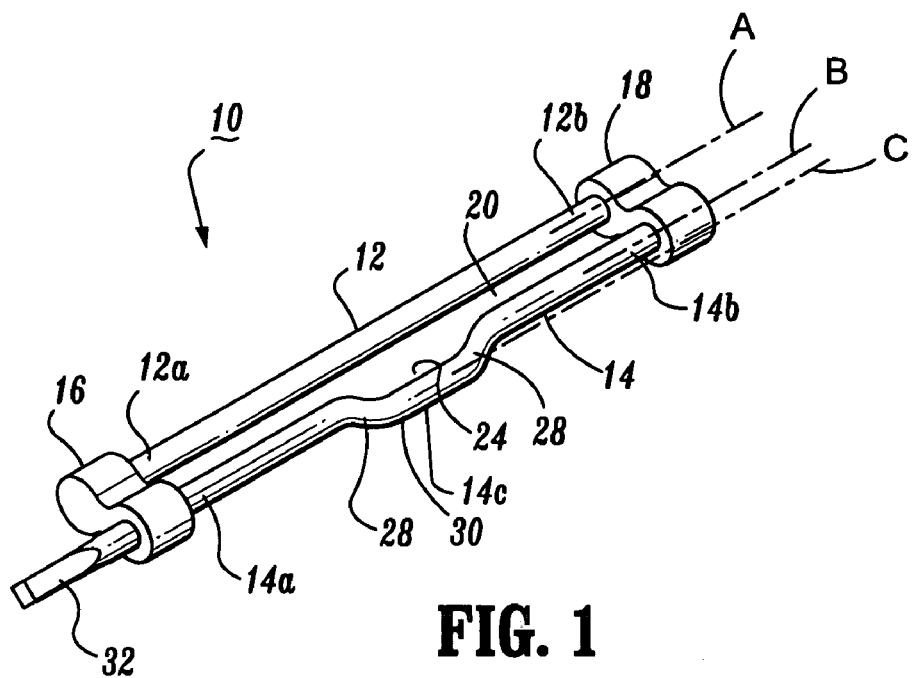
FIG. 1 is a top side perspective view of the presently disclosed gastric restrictor assembly.

FIG. 1 illustrates one embodiment of the presently disclosed gastric restrictor assembly shown generally as 10. Briefly, gastric restrictor assembly 10 includes a first longitudinal member 12, a second longitudinal member 14, a first connector 16 and a second connector 18. First and second connectors 16 and 18 support first and second longitudinal members 12 and 14 in spaced relation to define a channel 20.

Figure 2:
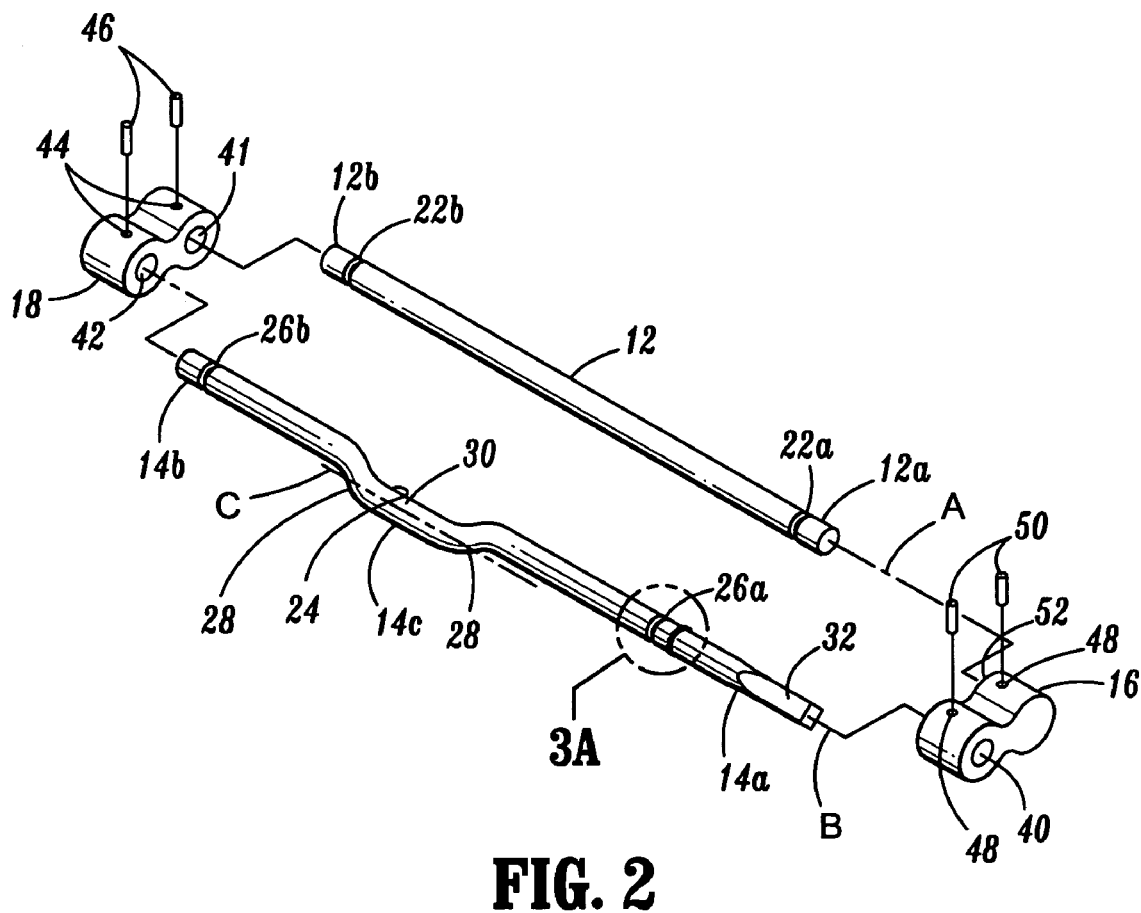
FIG. 2 is a top side perspective exploded view of the gastric restrictor assembly shown in FIG. 1.

Referring also to FIG. 2, first longitudinal member 12 may be a substantially rigid bar or rod which can be formed of metal, plastic or any other surgically approved material having the requisite strength requirements. First longitudinal member 12 defines a first longitudinal axis "A" and has a first end 12a and a second end 12b. In one embodiment, first and second ends 12a and 12b each have an annular groove 22a and 22b, respectively, formed thereabout to facilitate attachment of first longitudinal member 12 to first and second connectors 16 and 18, respectively, as will be discussed in further detail below.

Second longitudinal member 14 may be a substantially rigid bar or rod and also can be formed of any surgically approved material having the requisite strength requirements, e.g., metal, plastic, etc. Second longitudinal member 14 defines a second longitudinal axis "B" and has a first end 14a, a second end 14b, and an intermediate bend 14c or offset defining a recess 24. First and second ends 14a and 14b each include an annular groove 26a and 26b, respectively, for rotatably fastening first and second ends 14a and 14b of second longitudinal member 14 between first and second connectors 16 and 18 as will be discussed in further detail below. In one embodiment, intermediate bend 14c includes a pair of transverse or angled portions 28 and a base 30. Base 30 defines a third longitudinal axis "C" (FIG. 1) which is spaced from second longitudinal axis "B". It is contemplated that intermediate bend 14c may assume a multiplicity of other configurations, e.g., U-shape, semi-spherically shaped, circular etc.

Figure 3:
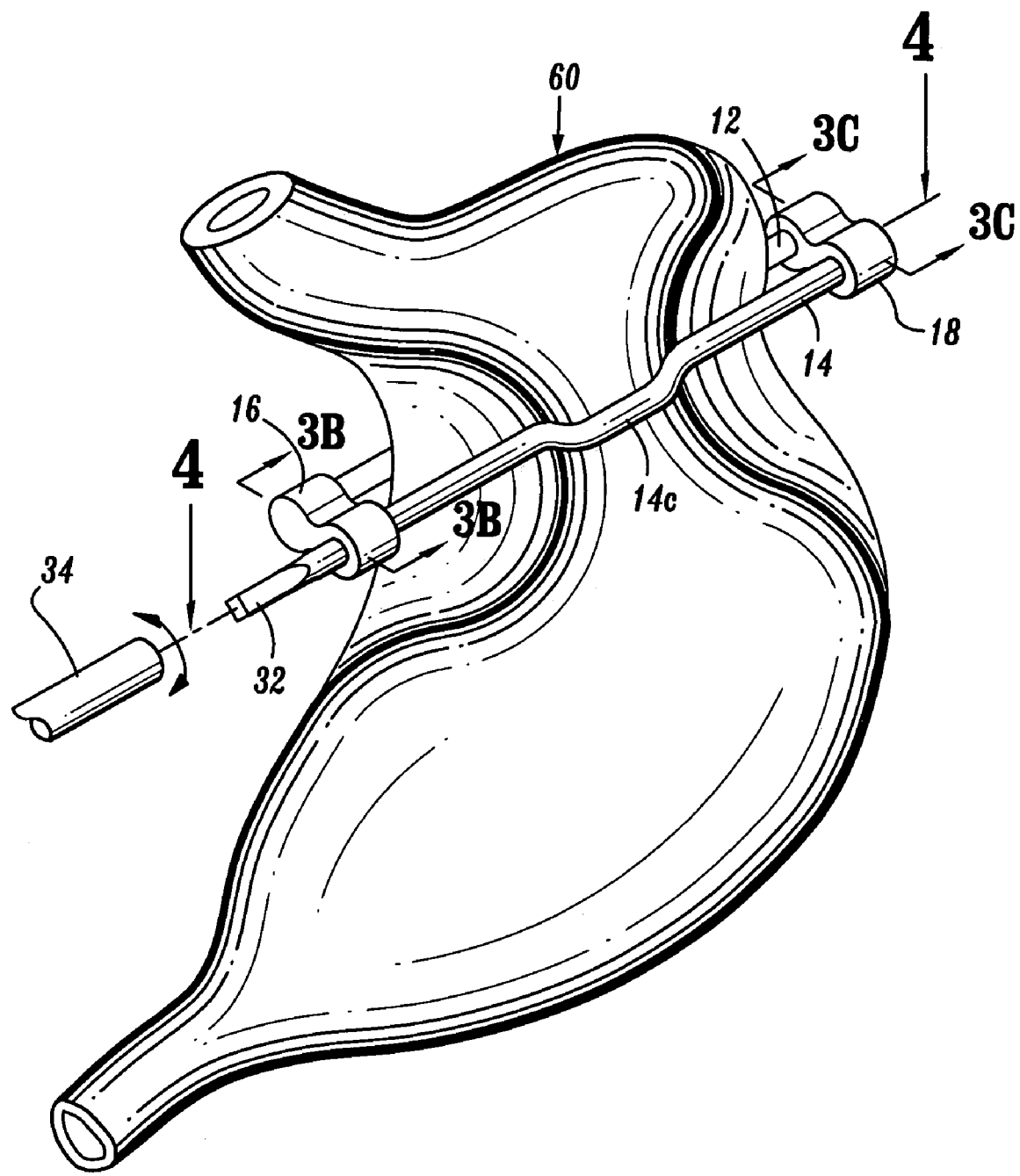
FIG. 3 is a top side perspective view of the gastric restrictor assembly shown in FIG. 1 positioned about a portion of the stomach.

First end 14a of second longitudinal member 14 includes engagement structure 32 configured to engage a positioning tool, e.g., wrench 34 (FIG. 3). Engagement structure 32 may include a hexagonal head for engaging the positioning tool. Alternately, any externally configured head or internally configured receptacle may be provided on the first end 14a of member 14 to engage a positioning tool. It is also contemplated that first end 14a of second longitudinal member 14 may include structure, e.g., a magnet, gears, a motor, etc. to facilitate rotation or transdermal actuation of second longitudinal member 14.

Figure 3A:
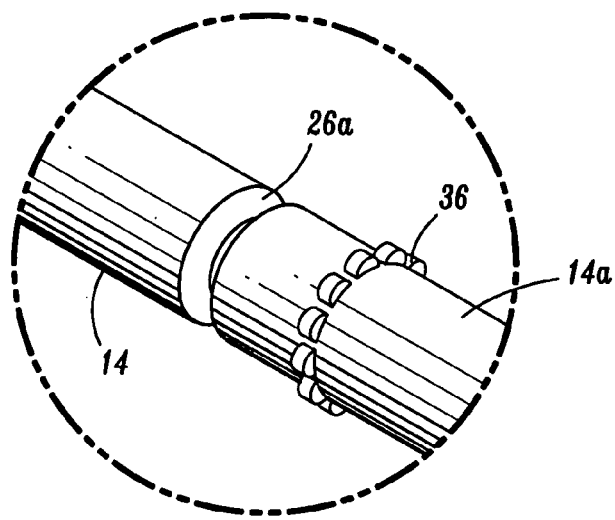
FIG. 3A is an enlarged view of the indicated area of detail shown in FIG. 2.
Figure 3B:
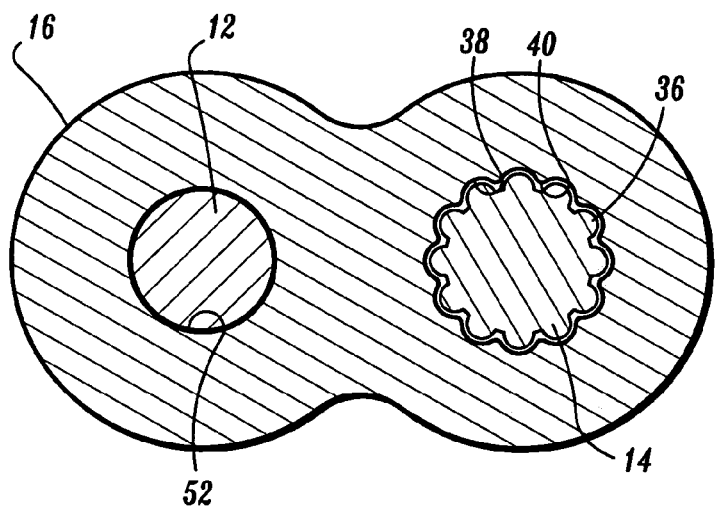
FIG. 3B is a cross-sectional view taken along section lines 3B-3B of FIG. 3.
Figure 3C:
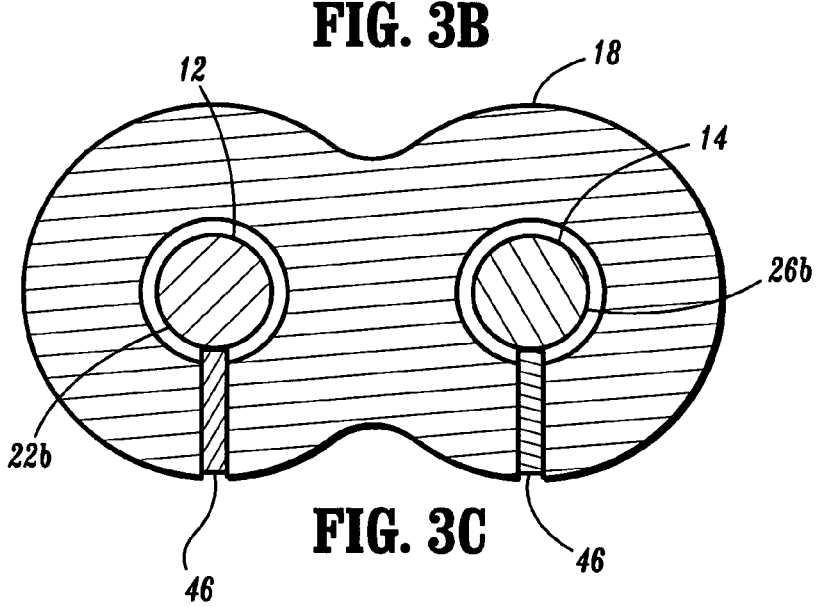
FIG. 3C is a cross-sectional view taken along section lines 3C-3C of FIG. 3.
Figure 4:
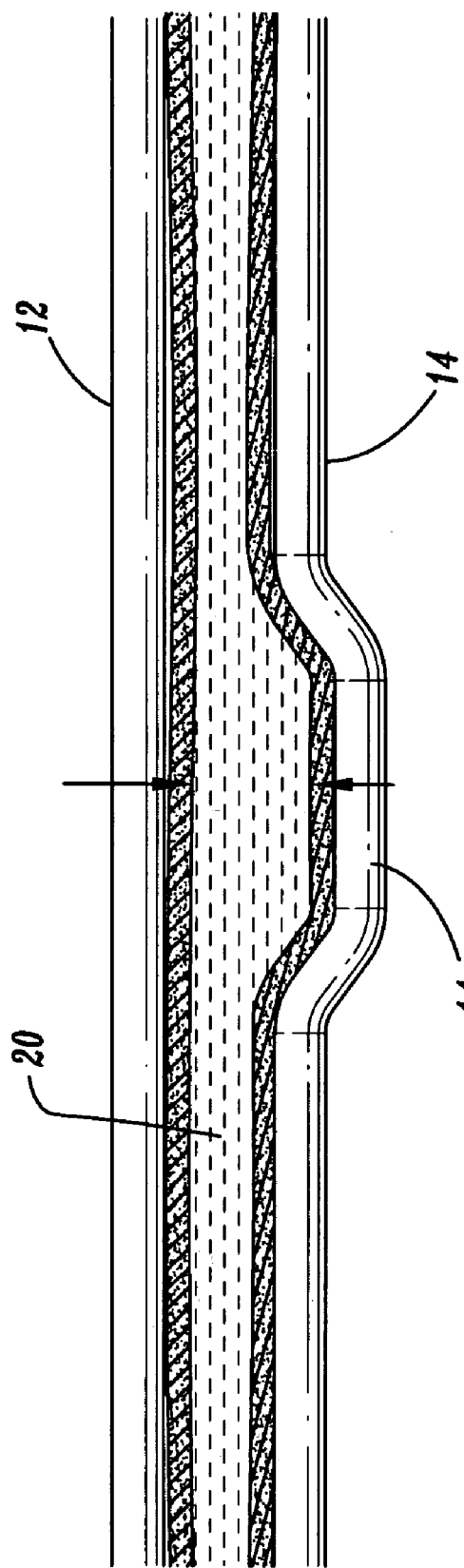
FIG. 4 is a cross-sectional view taken along section lines 4-4 of FIG. 3.

Referring also to FIGS. 3A and 3B, first end 14a of second longitudinal member 14 is also provided indexing structure such as a series of detents 36 which are annularly disposed about second longitudinal member 14. Detents 36 are configured to be received within recesses or grooves 38 (FIG. 3B) defined within a throughbore 40 of first connector 16 to releasably secure second longitudinal member 14 at a fixed position of rotation in relation to first longitudinal member. Upon application of a predetermined torque to second longitudinal member 14, the position of rotation of second longitudinal member 14 can be selectively varied. In one embodiment, detents 36 have a degree of resilience and are formed monolithically with second longitudinal member 14. In an alternate embodiment, detents 36 may be fastened about second longitudinal member 14 such as by overmolding, using adhesives or the like.

Second connector 18 includes first and second bores 41 and 42 dimensioned to receive second ends 12b and 14b, respectively, of first and second longitudinal members 12 and 14. Second connector 18 also includes a pair of holes 44 which are each dimensioned to receive a pin or screw 46. Holes 44 communicate with bores 41 and 42 such that pins 46 extend into annular grooves 22b and 26b of first and second longitudinal members 12 and 14 to rotatably secure the second ends 12b and 14b of first and second longitudinal members within bores 41 and 42 of second connector 18. Alternately, other fastening techniques may be used to secure members 12 and 14 to connector 18. In a like manner, first connector 16 includes holes 48 for receiving pins 50 to rotatably secure the first ends 12a and 14a of first and second longitudinal members 12 and 14, respectively, within bores 52 and 40 of first connector 16. Pins 50 are received within annular grooves 22a and 26a of first and second longitudinal members 12 and 14 to rotatably secure first ends 12a and 14a within bores 52 and 40 of first connector 16. It is contemplated that first longitudinal member may be non-rotatably secured between first and second connectors 16 and 18.

Figure 5:
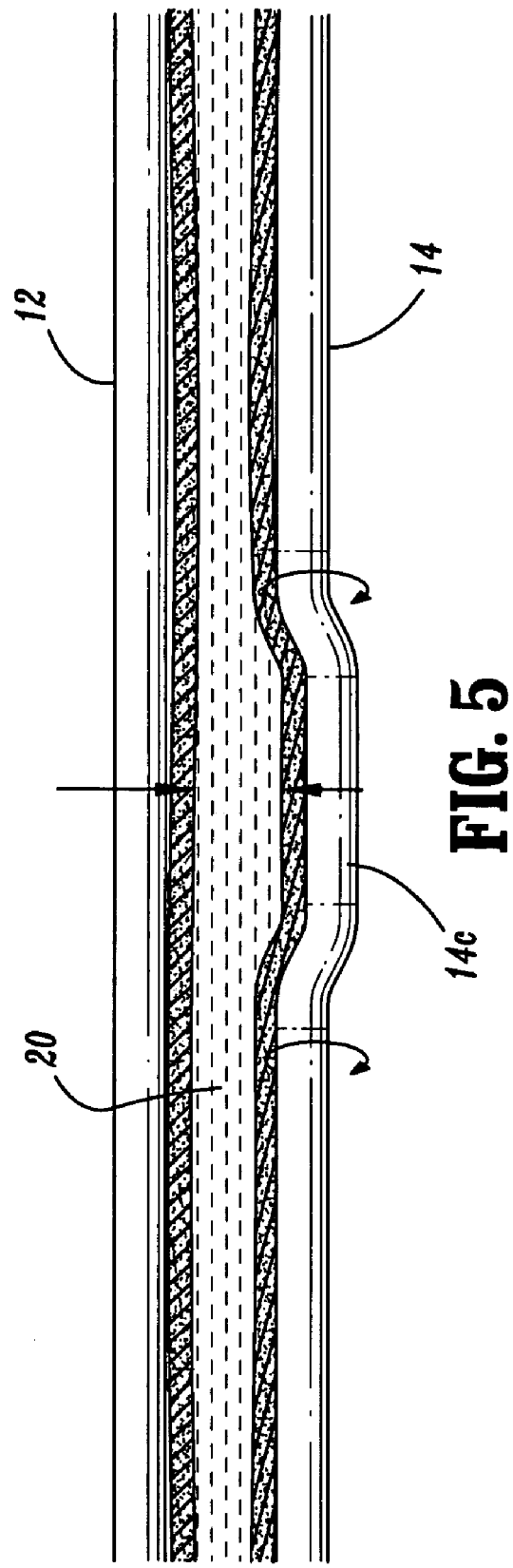
FIG. 5 is a cross-sectional view taken along section lines 4-4 of FIG. 3 after the second longitudinal member has been rotated to reduce the width of the channel between the first and second longitudinal members.
Figure 6:
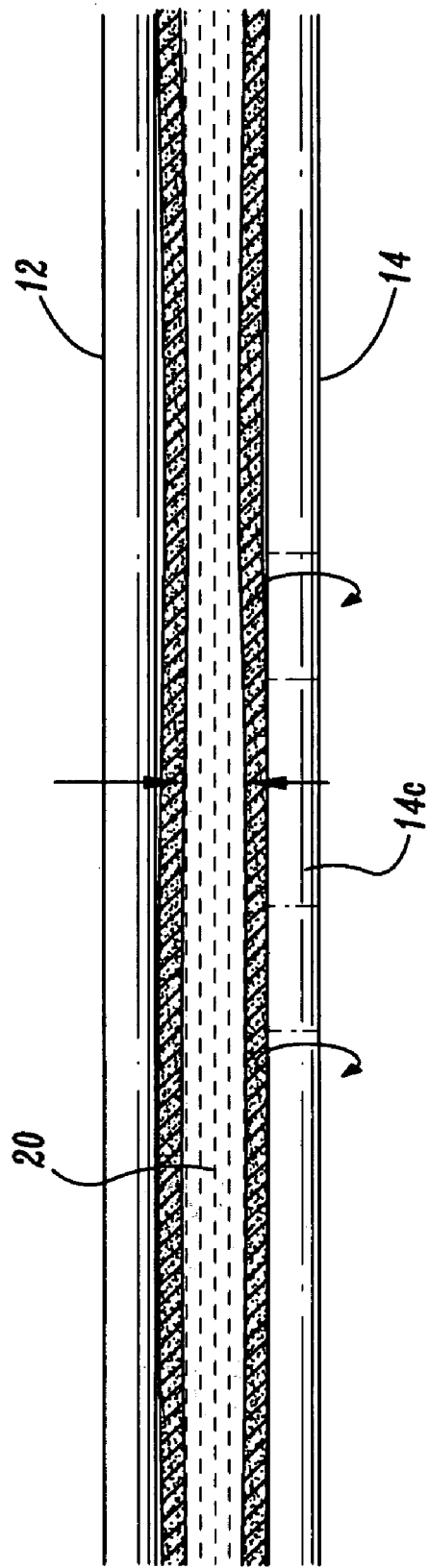
FIG. 6 is a cross-sectional view taken along section lines 4-4 of FIG. 3 after the second longitudinal member has been rotated to further reduce the width of the channel between the first and second longitudinal members.
Figure 7:
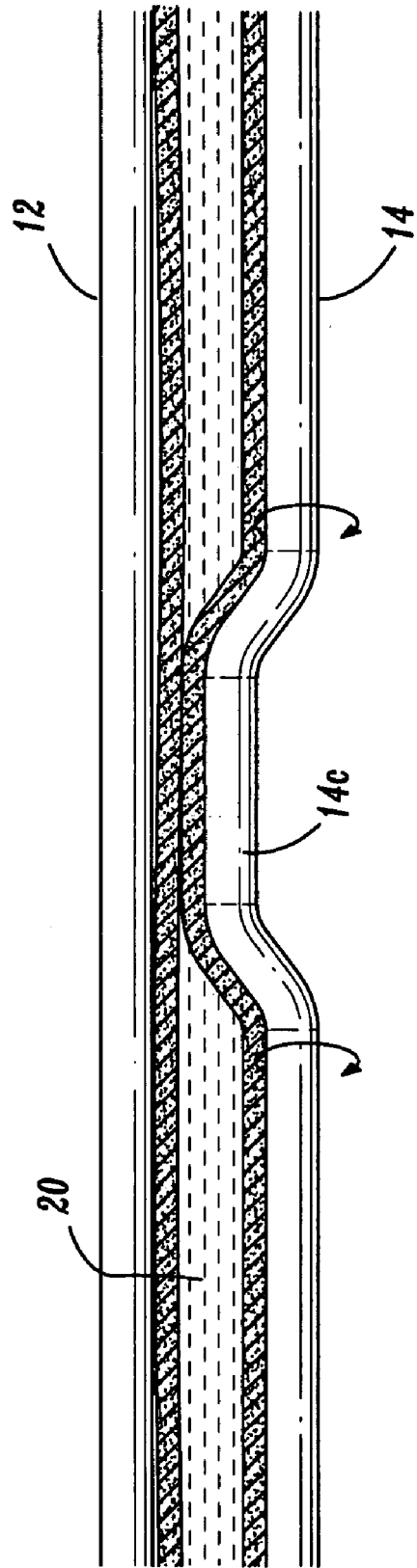
FIG. 7 is a cross-sectional view taken along section lines 4-4 of FIG. 3 after the second longitudinal member has been rotated to further reduce the width of the channel between the first and second longitudinal members.

Referring to FIGS. 3-7, in use, gastric restrictor assembly 10 is positioned about the stomach 60 of a patient during an open surgical procedure or laparoscopic surgical procedure. This is accomplished by first accessing the stomach 60 and positioning first longitudinal member 12 on one side of the stomach and second longitudinal member 14 on an opposite side of stomach 60. Next, connectors 16 and 18 are secured to the first and second ends of the first and second longitudinal members using pins or screws 46 and 50. As illustrated in FIGS. 4-7, the space between first longitudinal member 12 and second longitudinal member 14 defines a channel 20 in which stomach 60 is positioned. The width of channel 20 can be adjusted by rotating second longitudinal member 14 about the second longitudinal axis B (FIG. 1) using positioning tool 34 (FIG. 3). In the fully spaced position, intermediate bend 14c is rotated to a position 180° from first longitudinal member 12 (See FIG. 4). In its fully closed position, intermediate bend 14c is rotated to a position adjacent first longitudinal member 12 (FIG. 7) (180° from the fully open position). FIGS. 5 and 6 illustrate intermediate positions of second longitudinal member 14.

It will be understood that various modifications may be made to the embodiments disclosed herein. For example, intermediate bend 14c need not be centrally located on second longitudinal member 14 but rather may be positioned anywhere along its length. Further, multiple bends (2, 3, etc.) may be provided in second longitudinal member. It is also contemplated that one or both of the first and second longitudinal members may be formed of a non-rigid or less rigid material. Therefore, the above description should not be construed as limiting, but merely as exemplifications of embodiments. Those skilled in the art will envision other modifications within the scope and spirit of the claims appended hereto.

What is claimed is:

1. A gastric restrictor assembly comprising:
a first longitudinal member defining a first longitudinal axis (A);
a second longitudinal member defining a second longitudinal axis (B), the second longitudinal member having an offset formed therein, the offset defining a recess with the second longitudinal axis;
a first connector adapted to secure a first end of each of the first and second longitudinal member in spaced relation;
a second connector being adapted to secure a second end of each of the first and second longitudinal members in spaced relation;
wherein the first and second longitudinal members are supported in spaced relation to define a channel having a first width defined between the first and second longitudinal axes and a second width between the first longitudinal axis and the offset, wherein the first and second longitudinal axes are fixed in relation to each other and the second longitudinal member is rotatable about the second longitudinal axis while the first and second longitudinal axes are in fixed relation to reposition the offset in relation to the first longitudinal axis.

2. A gastric restrictor assembly according to claim 1, wherein the first end of the second longitudinal member includes engagement structure adapted to engage a positioning tool for adjusting the distance between the offset and the first longitudinal axis.

3. A gastric restrictor assembly according to claim 1, wherein the first and second ends of the second longitudinal member each include an annular channel and each of the first and second connectors includes a hole for receiving a pin, each pin being positioned within a respective hole in the first and second connectors and extending into a respective one of the annular channels to rotatably secure one of the first and second ends of the second longitudinal member to a respective one of the first and second connectors.

4. A gastric restrictor assembly according to claim 3, wherein the first connector includes a throughbore dimensioned to slidably receive the first end of the second longitudinal member, the first end of the second longitudinal member including engagement structure to facilitate engagement by a positioning tool.

5. A gastric restrictor assembly according to claim 1, wherein the first end of the second longitudinal member includes at least one recess and the first connector includes at least one detent positioned to be selectively received in the at least one recess to releasably secure the second longitudinal member in a fixed position of rotation.

6. A gastric restrictor assembly according to claim 5, wherein the first and second longitudinal members are substantially rigid rods.

7. A gastric restrictor assembly according to claim 6, wherein the offset includes first and second angled portions and a longitudinal portion, the longitudinal portion being substantially parallel to the second longitudinal axis.

8. A gastric restrictor assembly according to claim 5, wherein the at least one recess includes a plurality of recess.

9. A gastric restrictor assembly according to claim 8, wherein the at least one detent includes a plurality of detents.

10. A method of restricting a portion of the digestive tract comprising the following steps:
  i) providing a gastric restrictor assembly including a first longitudinal member defining a first axis and a second longitudinal member defining a second axis and including an offset, the second longitudinal member being supported in spaced relation to the first longitudinal member to define a channel having a first width defined between the first axis and second axis and a second width defined between the first axis and the offset;
  ii) positioning the gastric restrictor assembly about a portion of the digestive tract; and
  iii) repositioning the second longitudinal member by rotating the second longitudinal member about the second longitudinal axis and moving the offset in relation to the first longitudinal member to change the second width.

11. A method according to claim 10, wherein the second longitudinal member is rotatable about the second axis.

12. A method according to claim 11, wherein the portion of the digestive tract is the stomach.

13. A method according to claim 10, wherein the portion of the digestive tract is the stomach.

14. A gastric restrictor assembly comprising:
  a first longitudinal member defining a first longitudinal axis;
  a second longitudinal member defining a second longitudinal axis which is fixed in relation to the first longitudinal axis, the second longitudinal member having an offset formed therein, the offset defining a recess with the second longitudinal axis;
  wherein the first and second longitudinal members are supported in spaced relation to define a channel having a first width defined between the first and second longitudinal axes and a second width between the first longitudinal axis and the offset, the second longitudinal member being rotatable about the second longitudinal axis in relation to the first longitudinal member while the first and second axes remain fixed to selectively change the second width.

15. A gastric restrictor assembly according to claim 14, wherein the second longitudinal member is rotatably secured between a first connector and a second connector such that the distance between the offset and the first longitudinal axis is adjustable.

16. A gastric restrictor assembly according to claim 15, wherein the first end of the second longitudinal member includes engagement structure adapted to engage a positioning tool for adjusting the distance between the offset and the first longitudinal axis.

17. A gastric restrictor assembly according to claim 15, wherein the first and second ends of the second longitudinal member each include an annular channel and each of first and second connectors includes a hole for receiving a pin, each pin being positioned within a respective hole in the first and second connectors and extending into a respective one of the annular channels to rotatably secure one of the first and second ends of the second longitudinal member to a respective one of the first and second connectors.

* * * * *